(12) United States Patent
Forsyth et al.

(10) Patent No.: US 8,686,134 B2
(45) Date of Patent: *Apr. 1, 2014

(54) IONIC LIQUIDS

(75) Inventors: Stewart Forsyth, Wingate (GB);
Kenneth Richard Seddon, Donaghadee (IE); Keith Whiston, Darlington (GB)

(73) Assignee: Invista North America S.A R.L., Wilmington, DE (US)

( * ) Notice: Subject to any disclaimer, the term of this patent is extended or adjusted under 35 U.S.C. 154(b) by 49 days.

This patent is subject to a terminal disclaimer.

(21) Appl. No.: 13/186,943

(22) Filed: Jul. 20, 2011

(65) Prior Publication Data

US 2012/0190844 A1  Jul. 26, 2012

Related U.S. Application Data

(62) Division of application No. 12/128,893, filed on May 29, 2008, now Pat. No. 8,088,917.

(60) Provisional application No. 60/941,406, filed on Jun. 1, 2007.

(51) Int. Cl.
| | |
|---|---|
| *C07D 223/00* | (2006.01) |
| *C07D 223/14* | (2006.01) |
| *C07D 487/00* | (2006.01) |
| *C07D 491/00* | (2006.01) |
| *C07D 513/00* | (2006.01) |
| *C07D 405/00* | (2006.01) |
| *C07D 409/00* | (2006.01) |
| *C07D 223/04* | (2006.01) |
| *C07D 295/00* | (2006.01) |
| *C09K 3/00* | (2006.01) |

(52) U.S. Cl.
USPC .......... 540/484; 540/543; 540/596; 540/611; 540/612; 252/182.12

(58) Field of Classification Search
USPC .......... 540/484, 543, 596, 611, 612; 252/182.12
See application file for complete search history.

(56) References Cited

U.S. PATENT DOCUMENTS

| | | | |
|---|---|---|---|
| 3,845,211 | A | 10/1974 | Prugh |
| 3,903,286 | A | 9/1975 | Prugh |
| 4,086,237 | A | 4/1978 | Daum et al. |
| 4,557,838 | A | 12/1985 | Nichols et al. |
| 5,468,900 | A | 11/1995 | Moran, Jr. et al. |
| 5,521,261 | A | 5/1996 | Hofer et al. |
| 7,157,588 | B2 | 1/2007 | Harmer et al. |
| 2006/0223995 | A1 | 10/2006 | Uchimura et al. |

FOREIGN PATENT DOCUMENTS

| | | |
|---|---|---|
| JP | 2005347176 | 12/2005 |
| WO | WO2006/072785 | 7/2006 |
| WO | WO2006/136529 | 12/2006 |

OTHER PUBLICATIONS

Milli et al. Zeolite synthesis in the presence of azonia-spiro compounds as structure-directing agents. Microporous and Mesoporous Materials 24 (1998) 199-211.*
J. Org. Chem., 1995, 60, 8371-8374.

* cited by examiner

*Primary Examiner* — Harold Pyon
*Assistant Examiner* — Tanisha Diggs
(74) *Attorney, Agent, or Firm* — Robert B. Furr, Jr.; Stanislaus Aksman; Nicoletta Kennedy

(57) ABSTRACT

The invention relates to an ionic liquid composition and a method for preparing the ionic liquid. The ionic liquid comprises a cation containing the Formula I, as herein disclosed, and wherein: n is 2, $R^1$ is selected from the group consisting of: H, $C_1$-$C_{12}$ alkyl, aryl or together with $R^2$ may form a heterocyclic ring, and $R^2$ is selected from the group consisting of: H, $C_1$-$C_{12}$ alkyl, aryl or together with $R^1$ may form a heterocyclic ring, and $R^3$ is selected from the group consisting of hydrogen and $C_1$-$C_{12}$ alkyl, and wherein $R^1$ and $R^2$ are not simultaneously selected from hydrogen.

5 Claims, No Drawings

IONIC LIQUIDS

The present invention relates to heterocyclic compounds that are useful as ionic liquids. This application is a divisional of application Ser. No. 12/128,893, which claims benefit of priority from Provisional Application No. 60/941,406, filed Jun. 1, 2007. This application hereby incorporates by reference Provisional Application No. 60/941,406 in its entirety.

BACKGROUND

1. Field of the Invention

An ionic liquid is a liquid that contains essentially only ions, i.e., molten salts, although some ionic liquids are in a dynamic equilibrium wherein the majority of the liquid is made up of ionic species rather than molecular species. As used herein, the term "ionic liquids" refers to liquids composed of ions. In one embodiment, the term "ionic liquids" refers to liquids composed of ions which are liquid at or below about 100° C.

Ionic liquids generally consist of salts of organic cations. The organic cations are generally bulky and asymmetric such as N-methyl-N-alkylpyrrolidinium, N-alkyl-pyridinium, 1-alkyl-3-alkylimidazolium, and tetraalkylammonium ions. A number of different anions may be employed, from halides to inorganic anions such as hexafluorophosphate and tetrafluoroborate and to large organic anions like bis(trifluoromethanesulfonyl)imide, trifluoroacetate or toluene-4-sulfonate. For instance, U.S. Pat. No. 7,157,588 B2 teaches compositions based on N-substituted pyrrolidinones having a pendant ammonium cation separated from the pyrrolidone ring by a variable length alkyl spacer. WO 2006/136529 teaches pyrazolium alkylsulfates and a method for their production.

The object of the present invention is to provide novel ionic liquid compositions.

2. Description of the Invention

According to the present invention there is provided an ionic liquid comprising a cation according to Formula I:—

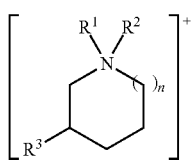

Formula I wherein:
n is 2,
$R^1$ is selected from the group consisting of: H, $C_1$-$C_{12}$ alkyl, aryl or together with $R^2$ may form a heterocyclic ring, and
$R^2$ is selected from the group consisting of: H, $C_1$-$C_{12}$ alkyl, aryl or together with $R^1$ may form a heterocyclic ring, and
$R^3$ is selected from the group consisting of hydrogen and $C_1$-$C_{12}$ alkyl,
wherein $R^1$ and $R^2$ are not simultaneously selected from hydrogen.

In a preferred embodiment, $R^3$ is hydrogen.

As used herein, the term "alkyl" means a branched or unbranched, cyclic or acyclic, saturated or unsaturated (i.e., alkenyl or alkynyl)hydrocarbyl radical which may be substituted or unsubstituted. Where cyclic, the alkyl group is preferably $C_3$ to $C_{12}$, more preferably $C_5$ to $C_{10}$, more preferably $C_5$, $C_6$ or $C_7$. Where acyclic, the alkyl group is preferably $C_1$ to $C_{10}$, more preferably $C_1$ to $C_6$, more preferably methyl, ethyl, propyl (n-propyl or isopropyl), butyl (n-butyl, isobutyl or tertiary-butyl) or pentyl (including n-pentyl and iso-pentyl), more preferably methyl. It will be appreciated therefore that the term "alkyl" as used herein includes alkyl (branched or unbranched), alkenyl (branched or unbranched), alkynyl (branched or unbranched), cycloalkyl, cycloalkenyl and cycloalkynyl.

An alkyl group may be substituted with one or more substituents wherein possible substituents include alkyl; aryl; heteroaryl; arylalkyl (e.g., substituted and unsubstituted benzyl, including alkylbenzyl); halogen atoms and halogen-containing groups such as haloalkyl (e.g., trifluoromethyl) or haloaryl (e.g., chlorophenyl); alcohols (e.g., hydroxy, hydroxyalkyl, hydroxyaryl, (aryl)(hydroxy)alkyl); ethers (e.g., alkoxy, aryloxy, alkoxyalkyl, aryloxyalkyl, alkoxyaryl, aryloxyaryl) and carboxyl (e.g., carboxaldehyde, alkyl- or aryl-carbonyl, carboxy, carboxyalkyl or carboxyaryl), amide and nitrile.

Subject to the constraints of formula I above, $R^1$ and $R^2$ may be the same or different and in one embodiment are different.

$R^1$ and $R^2$ may together form a heterocyclic ring comprising at least 2 carbon atoms and one nitrogen atom.

As used herein, a "heterocyclic ring" refers to a monocyclic, saturated or partially unsaturated, heterocyclic radical in which the ring contains at least 3 members, preferably 3-12 members, more preferably 5 or 6 members, of which one member is a N atom and at least two of the other members are C atoms. Preferably the heterocyclic ring is unsubstituted. By way of non-limiting example, suitable N-heterocyclyl groups include aziridinyl, azetidinyl, pyrrolidinyl, piperidyl, azepanyl, azocanyl, azonanyl, azecanyl, azacycloundecanyl and azacyclododecanyl.

As used herein, the term "aryl" means a carbocyclic aromatic group, such as phenyl or naphthyl (preferably phenyl).

The aryl group may be substituted with one or more substituents wherein possible substituents include alkyl; aryl; heteroaryl; arylalkyl (e.g., substituted and unsubstituted benzyl, including alkylbenzyl); halogen atoms and halogen-containing groups such as haloalkyl (e.g., trifluoromethyl) or haloaryl (e.g., chlorophenyl); alcohols (e.g., hydroxy, hydroxyalkyl, hydroxyaryl, (aryl)(hydroxy)alkyl); ethers (e.g., alkoxy, aryloxy, alkoxyalkyl, aryloxyalkyl, alkoxyaryl, aryloxyaryl) and carboxyl (e.g., carboxaldehyde, alkyl- or aryl-carbonyl, carboxy, carboxyalkyl or carboxyaryl), amide and nitrile. Preferably the aryl group is unsubstituted.

As used herein, the term "heteroaryl" means an aromatic group containing one or more heteroatom(s) preferably selected from N, O and S, such as pyridyl, pyrrolyl, quinolinyl, furanyl, thienyl, oxadiazolyl, thiadiazolyl, thiazolyl, oxazolyl, isoxazolyl, pyrazolyl, triazolyl, imidazolyl, pyrimidinyl, indolyl, pyrazinyl or indizolyl.

As used herein, the term "halogen" means a fluorine, chlorine, bromine or iodine radical.

In one embodiment, neither $R^1$ nor $R^2$ is selected from hydrogen.

In one embodiment, both $R^1$ and $R^2$ are optionally substituted $C_1$-$C_{12}$ alkyl groups. Preferably, $R^1$ is an optionally substituted $C_1$-$C_6$ alkyl group and/or $R^2$ is an optionally substituted $C_1$-$C_6$ alkyl group. Preferably the $R^1$ and $R^2$ alkyl groups are unsubstituted. Preferably $R^1$ is an unsubstituted butyl group. Preferably $R^2$ is a methyl group. Preferably the ionic liquid cation is of formula Ia or Ib, i.e., 1-butyl-1-methyl-azepanium or 1-butyl-1,3-dimethylpiperidinium, respectively:

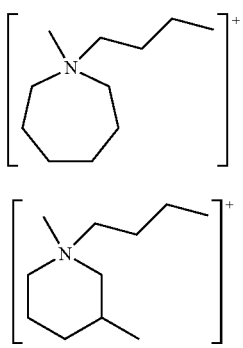

Formula Ia

Formula Ib

In a further embodiment, one of $R^1$ and $R^2$ is an optionally substituted $C_1$-$C_{12}$ alkyl group and the other is an optionally substituted aryl group. Preferably the optionally substituted alkyl group is an optionally substituted $C_1$-$C_6$ alkyl group. Preferably the alkyl group is unsubstituted. Preferably the aryl group is unsubstituted.

In a further embodiment, both $R^1$ and $R^2$ are optionally substituted aryl groups. Preferably the aryl groups are unsubstituted.

In a further embodiment, $R^1$ and $R^2$ together form a heterocyclic ring. Preferably the heterocyclic ring is unsaturated. Preferably the heterocyclic ring is an unsaturated ring with 5 or 6 members. In this embodiment, preferably the ionic liquid cation is of formula Ic, 6-azonia-spiro[5,6]dodecane:

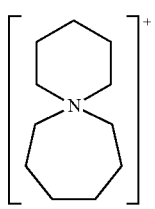

Formula Ic

In a further embodiment, the ionic liquid comprises one or more different cations all represented by Formula I.

In a further embodiment, the ionic liquid comprises one or more different cations all represented by Formula I and one or more further cations selected from the group consisting of imidazolium, pyrazolium, oxazolium, thiazolium, triazolium, pyridinium, pyridazinium, pyrimidinium, phosphonium and pyrazinium, wherein the further cation or each of said further cation(s) is substituted with a substituent group selected from $C_1$-$C_{12}$ alkyl or aryl as defined herein, preferably $C_1$-$C_{12}$ alkyl.

The ionic liquid according to formula I comprises an anion, $X^-$, preferably selected from the group consisting of: bis(trifluoromethylsulphonyl)imide; dicyanamide; hexahalophosphates (preferably hexafluorophosphate or hexachlorophosphate); tetrahaloborates (preferably tetrafluoroborate or tetrachloroborate); halides; nitrates; sulfates; phosphates; carbonates; sulfonates; carboxylates and silicates.

The sulfates may be selected from the group consisting of sulfate, hydrogen sulfate, alkyl or aryl sulfate, alkyl or aryl sulfonates, trifluoromethanesulfonate, and toluene-4-sulfonate, alkyl or aryl oxoanion sulfates. Preferably the oxoanion sulfates are selected from persulfate ($SO_5^{2-}$), sulfite ($SO_3^{2-}$), hyposulfite ($SO_2^{2-}$), peroxydisulfite ($S_2O_8^{2-}$).

The phosphates may be selected from the groups consisting of: phosphate; hydrogen phosphate; dihydrogen phosphate, alkyl or aryl phosphate, alkyl or aryl phosphonates, alkyl or aryl phosphinates, other oxoanion phosphates and metaphosphate.

The carbonates may be selected from the group consisting of carbonate and hydrogen carbonate, alkyl or aryl carbonates and other oxoanion carbonates.

The carboxylates may be selected from the group consisting of: alkylcarboxylates; arylcarboxylates and ethylenediaminetetraacetate.

As used herein, the term "alkylcarboxylates" refers to alkyl compounds with one or more carboxylate groups, preferably one, two or three carboxylate groups. Alkylcarboxylates include formate; acetate, propanoate, butanoate, pentanoate, hexanoate, heptanoate, octanoate, nonanoate, decanoate, oxalate; succinate; crotonate; fumarate. The term "alkylcarboxylates", as used herein, further includes carboxylates wherein the alkyl group is substituted with the substituent groups referred to herein and therefore further includes glycolate; lactate; tartrate; hydrogen tartrate; malate; citrate; trifluoroacetate; pentafluoropropanoate; heptafluorobutanoate; mandelate; and phenylacetate As used herein, the term "arylcarboxylates" refers to aryl compounds with one or more pendant carboxylate groups, preferably one, two or three carboxylate groups. Arylcarboxylates include benzoate; benezenedicarboxylate; benzenetricarboxylate; benzenetetracarboxylate; chlorobenzoate; fluorobenzoate; pentachlorobenzoate; pentafluorobenzoate and salicylate.

Preferably $X^-$ is dicyanamide or bis(trifluoromethanesulfonyl)imide.

Preferably, the ionic liquid comprising the cation of formula I and the anion $X^-$ is selected from the group consisting of 1-butyl-1-methyl-azepanium bis(trifluoromethanesulfonyl)imide, 1-butyl-1-methyl-azepanium dicyanamide, 6-azonia-spiro[5,6]dodecane bis(trifluoromethanesulfonyl)imide, 6-azonia-spiro[5,6]dodecane dicyanamide, 1-butyl-1,3-dimethylpiperidinium bis(trifluoromethanesulfonyl)imide and 1-butyl-1,3-dimethylpiperidinium dicyanamide.

According to a further aspect of the present invention there is provided a method for the preparation of an ionic liquid according to formula I wherein the method comprises at least one N-substitution of the compound of formula II:

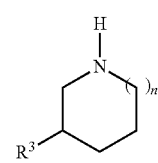

Formula II wherein:
n is 1 or 2,
$R^3$ is selected from the group consisting of hydrogen and $C_1$-$C_{12}$ alkyl, and
wherein when n is 1, $R^3$ is $C_1$-$C_{12}$ alkyl, preferably methyl.

In a preferred embodiment, if n=2, then $R^3$ is hydrogen.

As used herein, the step of N-substitution is an N-alkylation or N-arylation step and comprises contacting an N-substitution agent (i.e., an N-alkylating or N-arylating agent) with the compound of Formula II. Such synthetic procedures are well known in the art and may be carried out using any method known to the skilled person. In a preferred embodiment, the N-substitution step is an N-alkylation. A non-limiting example of the N-alkylation of azepane is described in the Journal of Organic Chemistry, Vol. 60, No. 26, 1995, 8371-8374. The N-substitution steps are described herein below with reference to N-alkylation although it will be appreciated that corresponding N-arylation steps are available to the skilled person.

The or each N-alkylation step(s) may be carried out with any $C_1$-$C_{12}$ alkylating reagent that is capable of quaternarising the amine nitrogen of formula II. Preferably the or each N-alkylation step is carried out using $C_1$-$C_{12}$ alkylating agent(s) selected from the group consisting of $C_1$-$C_{12}$ alkylating agents (e.g., alkyl halides, alkyl sulfonates or alkyl sulfates). The corresponding N-arylation reactions can be carried out using aryl sulfonates or aryl sulfates.

Preferably, the or each N-substitution reaction(s) may be carried out in an inert solvent, such as acetonitrile, acetone, methanol or dichloromethane In one embodiment, a single N-substitution step is carried out. The ionic liquid produced using the method of this embodiment has the formula described by formula I, wherein $R^1$ or $R^2$ is hydrogen.

In a further embodiment, two N-substitution steps are carried out. The ionic liquid produced using the method of this embodiment has the formula described by formula I, wherein neither $R^1$ nor $R^2$ is hydrogen.

In the embodiment comprising two N-substitution steps, both N-substitution steps may be carried out using the same N-substitution agent. Preferably, different N-substitution agents are used for each N-substitution step.

The two N-substitution steps may be carried out sequentially or simultaneously and are preferentially carried out sequentially.

Preferably, the two N-substitution steps are carried out sequentially with different N-substitution agents. Preferably, the first N-substitution step is carried out with the N-alkylating agent butyl bromide. Preferably the second N-substitution step is carried out with the N-alkylating agent methyl iodide.

Preferentially the single or first N-substitution step is carried out at a temperature below about 100° C., more preferably below about 75° C., more preferably below about 50° C., more preferably below about 20° C.

In the embodiment where there are two N-substitution steps, preferably the two N-substitution steps are carried out sequentially. The second N-substitution step is carried out at a temperature below about 100° C., more preferably below about 75° C., more preferably below about 50° C., more preferably below about 20° C. Preferably, after the reagents are added the reaction mixture is warmed to a temperature from about 0° C. to about 100° C., more preferably from about 0° C. to about 75° C., more preferably from about 0° C. to about 50° C., more preferably about room temperature.

The anion component of the single or second N-substitution step may form the ionic liquid anion, $X^-$. Preferably the anion component of the single or second N-substitution is selected from the group consisting of halides, sulfonates and sulfates.

In an alternative embodiment, the method may additionally comprise the step of anion exchange of the N-substituted salt product. Prior to the anion exchange, excess N-substitution agent may be removed, for example, by evaporation. In addition, the N-substituted salt product may be washed with a solvent prior to the anion exchange step.

The anion exchange step comprises contacting the N-substituted solution product with an ion exchange agent, optionally in an inert atmosphere. Preferably the anion exchange step is carried out at a temperature of from about 0° C. to about 100° C., more preferably from 0° C. to about 75° C., more preferably from about 0° C. to about 50° C., more preferably about room temperature. Preferably the N-substituted solution product and the ion exchange agent are contacted and stirred for several hours (e.g., from about 0.5 to about 24 hours, preferably from about 1 to about 15 hours, more preferably from about 4 to about 12 hours). The ion exchange agent comprises an $X^-$ anion as defined above but which is different to the anion component of the single or second N-substitution step present in the product obtained from the single or second N-substitution step.

Preferably the ion exchange agent is a metal salt of the anion $X^-$, defined previously. Preferably, the metal is an alkali metal or an alkaline earth metal.

The optional anion exchange step is typically conducted in solution. Solvents use in the anion exchange reaction should be inert to the reactants and the products and include methanol, ethanol, acetone, acetonitrile and water, preferably water. In one embodiment, the choice of the appropriate solvent, or mixture of solvents, that will allow for separation of the composition comprising the desired anion from the composition comprising the less desired anion is well known in the art and is exemplified in example 1. The composition comprising the desired anion can then be recovered using a suitable technique such as evaporation or the reactant solvent, decantation, re-crystallisation and/or filtration.

In an alternative embodiment, the anion exchange agent may be contacted with the N-substituted salt product and mixed in a solvent for a period of time, i.e., more than about 5 hours. The composition comprising the desired anion can then be recovered using a suitable technique such as evaporation or the reactant solvent, decantation, re-crystallisation and/or filtration.

Preferably formula II represents a compound selected from the group consisting of azepane and 3-methylpiperidine.

In one embodiment, formula II may represent azepane. The azepane represented by formula II may be a by-product of the manufacture of 1,6-hexanediamine. In a further embodiment, formula II may represent 3-methylpiperidine. The 3-methylpiperidine represented by formula II may be a by-product of the manufacture of 2-methyl-1,5-pentanediamine. In these by-product embodiments, the 1,6-hexanediamine may be produced by the hydrogenation of hexanedinitrile and the 2-methyl-1,5-pentanediamine may be produced by the hydrogenation of 2-methyl-pentanedinitrile.

In this embodiment, the hydrogenation reactions are preferably carried out in the presence of hydrogen gas and a catalyst, e.g., an iron catalyst or a Raney cobalt catalyst. The hydrogenation reactions are preferably carried out at an elevated temperature (e.g., from about 30° C. to about 500° C., preferably from about 50° C. to about 350° C., preferably from about 80° C. to about 200° C., preferably from about 80° C. to about 150° C.). The hydrogenation reactions are preferably carried out at elevated pressure (e.g., from about 400 psig to about 8000 psig, preferably from about 1000 psig to about 6000 psig, preferably about 1500 psig to about 5000 psig, preferably from about 3000 psig to about 5000 psig). Preferably, when using an iron catalyst, the hydrogentation reaction is carried out at a temperature of from 80° C. to about 200° C., preferably about 140° C. and/or a pressure of from about 1500 psig to about 5000 psig, preferably about 4500 psig. Preferably, when using a Raney cobalt catalyst, the hydrogenation reaction is carried out at a temperature of from 80° C. to about 150° C., preferably about 115° C. and/or a pressure of from about 400 psig to about 2500 psig, preferably about 800 psig. Preferably the compound of formula II is separated from the product mixture, i.e., the crude 1,6-hexanediamine or 2-methyl-1,5-pentanediamine, by distillation at reduced pressure and elevated temperature.

According to a further aspect of the present invention there is provided the use of an ionic liquid of the present invention in a chemical method.

As used herein, the term "chemical method" refers to any method used in chemistry. Chemical methods of the present invention include separations, extractions and syntheses, and encompass for instance the use of ionic liquids as solvents and as catalysts, biocatalysts, and in enzyme processes. The chemical method of the present invention further encompass the use of ionic liquids in heat storage applications, fuel cells, battery fluids, polymerisation, catalysis, protein purification, metal deposition, and as lubricants and surfactants.

According to a chemical method as used herein, the ionic liquids of the applicant's disclosures relate also to their cathodic stability when used as an electrolyte, characterized by a higher decomposition voltage than aqueous electrolytes for example. This higher decomposition voltage is implied by the measure of their "electrochemical window." The electrochemical window of a substance is a voltage range between which the substance does not become oxidized nor reduced.

Electrochemical window is measured using cyclic voltammetry methods, methods commonly known to the skilled practioner. In brief, the cyclic voltammetry analysis conducted by varying the voltage between two electrodes through an electrolyte and measuring the change in current with respect to change in voltage. The resulting cyclic voltammogram is represented in a current (ampere) versus voltage applied (volt) plot. The ionic liquids reported herein, according to Formula Ia and Ib previously, when used with the bis(trifluoromethylsulphonyl)amide anion and measured on glass calomel (GC) against Ag/Ag+ reference electrode exhibit a window of stability, being neither oxidized nor reduced from −3.5 volts to +3.0 volts.

As a chemical method for the ILs herein disclosed, the electro-oxidation of depolymerization products from nylon 6 or nylon 66 is provided. According to the teachings of U.S. Pat. No. 5,468,900 to McKinney et al., herein incorporated in their entirety, the conversion of nylon 6 and/or nylon 6,6 to adipic acid through at least an electrochemical means for oxidation is provided. Mckinney et al. exemplify a variety of oxidation techniques from which 6-alkylamidohexanoic acid, to yield adipic acid, can be carried out by a variety of oxidation techniques, e.g., using air, oxygen or hydrogen peroxide. Alternatively, the oxidation can be carried out in a subsequent step after the depolymerization is complete. The oxidation may also be carried out electro-chemically. The depolymerization products may be isolated from the depolymerization reaction mixture and redissolved in a suitable solvent containing an electrolyte prior to electrolysis. Alternatively, an electrolyte may be added directly to the polymerization reaction mixture, avoiding the need for isolating the depolymerization products. Optionally, an oxidation catalyst may be added to the solution. The mixture being oxidized may be checked periodically and the process continued until substantial amounts of adipic acid have been produced. Alternatively, the oxidation may be continued until the theoretical number of coulombs have been passed. At that point the solvent can be removed and the adipic acid recovered from the mixture containing the other reaction product, alkylamide, by crystallization or by other means.

The Applicants believe that a chemical method employing the ionic liquids disclosed herein and having a high cathodic stability when used as an electrolyte and solvent may be used to electrochemically oxidize the same materials as disclosed by Mckinney et al. The chemical method proposes to convert nylon 6 and/or nylon 6,6 to adipic acid monomer by depolymerization with an aliphatic monocarboxylic acid to form alkylamides followed by an electrochemical oxidation of the alkylamides to adipic acid and performed using only the ionic liquid as a solvent and electrolyte, with an option to add mineral acids, such as: sulfuric acid and phosphoric acid.

The Applicants believe that the electrochemical oxidation of 6-acetamido-hexanoic acid, the primary acetylation product of nylon 6 can be carried using substantially an ionic liquid solvent as the electrolyte. Optionally, an acidic co-solvent, sulfuric acid, may be present to add conductivity of the resulting solution. Following the teachings of McKinney et al., the 6-acetamidohexanoic acid is placed in a single compartment electrolytic cell fitted with parallel platinum foil electrodes, one inch apart and is charged with 7 grams 6-acetamidohexanoic acid and 75 ml of the ionic liquid and 2 ml of concentrated sulfuric acid. The contents of the cell are stirred with a magnetic stirrer bar during the electrolysis. The electrodes are connected to an electrical circuit containing a suitable direct current power supply, an ammeter and a coulometer. The electrolysis is conducted at a current of 480 milliamperes at a cell voltage of 2.9 volts for a sufficient time to accumulate 8074 coulombs. At the end of such an experimental run a sample examined by GC/MS would reveal the major components to be 6-acetamidohexanoic acid, adipic acid and 5-formyl valeric acid. It is believed that the product mixture would be found to contain adipic acid and 6-acetamidohexanoic acid (as determined by quantitative analysis by calibrated liquid chromatography) at about a 50% conversion of 6-acetamidohexanoic acid to yield 70% adipic acid on a molar basis about a 70. % current efficiency.

In a manner similar to that above, it is expected that the electrochemical oxidation of N,N'-hexamethylene bisacetamide, the acetylation product of nylon 6,6. The same electrolysis apparatus as employed above is used. The cell is charged with 4 grams of N,N'-hexamethylene bisacetamide and 75 ml of the ionic liquid and 2 ml of concentrated sulfuric acid. The electrolysis is conducted at a current of 480 milliamperes at a cell voltage of 3.1 volts for a sufficient time to accumulate 8050 coulombs. It is expected that at the end of the run a sample examined by GC/MS would reveal the major components to be N,N'-hexamethylene bisacetamide, 6-acetamidohexanoic acid, adipic acid, 5-formyl valeric acid and 6-acetamidocaproaldehyde. At a 60% conversion of N,N'-hexamethylene bisacetamide, a 13% yield to 6-acetamidohexanoic acid and 18% yield to adipic acid on a molar basis is expected.

According to a further aspect of the present invention there is provided the use of azepane and 3-methylpiperidine as precursors in the formation of ionic liquids.

The invention is further illustrated by the following examples. It will be appreciated that the examples are for illustrative purposes only and are not intended to limit the invention as described above. Modification of detail may be made without departing from the scope of the invention.

EXAMPLES

Example 1

The first N-substitution of azepane was carried out using butyl bromide as an N-alkylating agent to form 1-butylazepane. An equimolar amount of butyl bromide was added dropwise to a solution of azepane in methanol keeping the temperature at 2° C. by an ice-water bath. The mixture was hydrolyzed with potassium carbonate, extracted with ether, and dried over $Na_2SO_4$. The solution was fractionally distilled at reduced pressure and the fraction with by 195° C. was collected. $^1$H-NMR (300 MHz, CDCl$_3$) δ 0.90 (t, 3H), 1.28 (sextet, 2H), 1.42 (m, 2H), 1.60 (broad m, 8H), 2.42 (m, 2H), 2.60 (m, 4H).

Following this, a second N-substitution was carried out on the 1-butylazepane using methyl iodide as an N-alkylating agent to form 1-butyl-1-methylazipanium iodide. A slight excess of methyl iodide was added dropwise to 1-butylazepane in dichloromethane keeping the temperature below 20° C. by an ice-water bath. The reaction mixture was then allowed to warm to room temperature and stirred until complete conversion of amine (as determined using $^1$H nmr). Diethyl ether was then added to the reaction mixture and the white precipitate filtered, washed with ether and dried in air. The white solid 1-butyl-1-methylazipinium iodide melted at 214° C. $^1$H-NMR (300 MHz, CDCl$_3$) δ 1.00 (t, 3H), 1.40 (m, 2H), 1.78 (m, 6H), 1.90 (m, 4H), 3.02 (s, 3H), 3.30 (m, 2H), 3.40 (m, 4H).

A slight excess of lithium bis[(trifluoromethyl)sulfonyl] imide dissolved in water was added to an aqueous solution of 1-butyl-1-methylazipinium iodide and stirred at room temperature for approximately 5 hours. The reaction mixture was transferred to a separating funnel and the heavy layer washed several times with water. The addition of a small amount of dichloromethane aided the separation of the aqueous and organic layer. The heavy organic layer was then evaporated to dryness leaving a pale yellow liquid, 1-butyl-1-methylazipinium bis[(trifluoromethyl)sulfonyl]imide. ES/MS 170 (Cation C$_{11}$H$_{24}$N), −280 (Anion C$_2$F$_6$NS$_2$O$_4$).

Example 2

1-butyl-1-methylazipanium iodide was formed according to example 1.

A slight excess of silver dicyanamide (freshly prepared from AgO and NaN(CN)$_2$) was added to an aqueous solution of 1-butyl-1-methylazipinium iodide and stirred at room temperature for several hours. The reaction mixture was filtered and the filtrate evaporated to dryness leaving a clear liquid, 1-butyl-1-methylazipinium dicyanamide. ES/MS 170 (Cation C$_{11}$H$_{24}$N), −66 (Anion C$_2$N$_3$).

Example 3

The first N-substitution of 3-methylpiperidine was carried out using butyl bromide as an N-alkylating agent to form 1-butyl-3-methylpiperidine. An equimolar amount of butyl bromide was added dropwise to a solution of 3-methylpiperidine in methanol keeping the temperature at 20° C. by an ice-water bath. The mixture was hydrolyzed with potassium carbonate, extracted with ether, and dried over Na$_2$SO$_4$. The solution was fractionally distilled at reduced pressure and the fraction with by 195° C. was collected. $^1$H-NMR (300 MHz, CDCl$_3$) δ 0.82 (d, 3H), 0.90 (t, 3H), 1.30 (m, 2H), 1.48 (m, 2H), 1.65 (m, 5H), 2.24 (m, 2H), 2.82 (m, 4H).

Following this, a second N-substitution was carried out on the 1-butyl-3-methylpiperidine using methyl iodide as an N-alkylating agent to form 1-butyl-1-methyl-3-methylpiperidinium iodide. A slight excess of methyl iodide was added dropwise to 1-butyl-3-methylpiperidine in dichloromethane keeping the temperature below 20° C. by an ice-water bath. The reaction mixture was then allowed to warm to room temperature and stirred until complete conversion of amine (as determined using $^1$H nmr). Diethyl ether was then added to the reaction mixture and the white precipitate filtered, washed with ether and dried in air. The white solid form 1-butyl-1-methyl-3-methylpiperidinium iodide melted at 204° C. $^1$H-NMR (300 MHz, CDCl$_3$) δ 1.00 (d, 3H), 1.02 (t, 3H), 1.48 (m, 2H), 1.82 (m, 2H), 2.10 (m, 5H), 3.28 (s, 3H), 3.60 (m, 2H), 3.70 (m, 4H).

A slight excess of lithium bis[(trifluoromethyl)sulfonyl] imide dissolved in water was added to an aqueous solution of form 1-butyl-1-methyl-3-methylpiperidinium iodide and stirred at room temperature for approximately 5 hours. The reaction mixture was transferred to a separating funnel and the heavy layer washed several times with water. The addition of a small amount of dichloromethane aided the separation of the aqueous and organic layer. The heavy organic layer was then evaporated to dryness leaving a pale yellow liquid, form 1-butyl-1-methyl-3-methylpiperidinium bis[(trifluoromethyl)sulfonyl]imide. ES/MS 170 (Cation C$_{11}$H$_{24}$N), −280 (Anion C$_2$F$_6$NS$_2$O$_4$).

Example 4

1-butyl-1-methyl-3-methylpiperidinium iodide was formed according to example 3.

A slight excess of silver dicyanamide (freshly prepared from AgO and NaN(CN)$_2$) was added to an aqueous solution of 1-butyl-1-methyl-3-methylpiperidinium iodide and stirred at room temperature for approximately 5 hours. The reaction mixture was filtered and the filtrate evaporated to dryness leaving a clear liquid, 1-butyl-1-methyl-3-methylpiperidinium dicyanamide. ES/MS 170 (Cation C$_{11}$H$_{24}$N), −66 (Anion C$_2$N$_3$).

Example 5

A slight excess of 1,5-dibromopentane was added dropwise to a solution of azepane and sodium hydroxide in water and stirred at reflux for several hours. The solution was then cooled to room temperature and diluted with aqueous sodium hydroxide. The reaction mixture was then extracted with chloroform, washed with water several times and evaporated to dryness to yield the white solid 6-azonia-spiro[5,6]dodecane bromide with a melting point of 260° C. $^1$H-NMR (300 MHz, D$_2$O) δ 1.50 (m, 6H, CH$_2$), 1.75 (m, 8H, CH$_2$), 3.20 (t, 4H, N—CH$_2$), 3.30 (t, 4H, N—CH$_2$).

A slight excess of lithium bis[(trifluoromethyl)sulfonyl] imide dissolved in water was added to an aqueous solution of 6-azonia-spiro[5,6]dodecane bromide and stirred at room temperature for several hours. The reaction mixture was transferred to a separating funnel and the heavy layer washed several times with water. The addition of a small amount of dichloromethane aided the separation of the aqueous and organic layer. The heavy organic layer was then evaporated to dryness leaving a pale yellow solid, 6-azonia-spiro[5,6]dodecane bis[(trifluoromethyl)sulfonyl]imide with a melting point of 96° C. ES/MS 168 (Cation C$_{11}$H$_{22}$N), −280 (Anion C$_2$F$_6$NS$_2$O$_4$).

Example 6

6-azonia-spiro[5,6]dodecane bromide was formed according to example 5.

A slight excess of silver dicyanamide (freshly prepared from AgO and NaN(CN)$_2$) was added to an aqueous solution of 6-azonia-spiro[5,6]dodecane bromide and stirred at room temperature for several hours. The reaction mixture was filtered and the filtrate evaporated to dryness leaving a white solid, 6-azonia-spiro[5,6]dodecane dicyanamide with a melting point of 148° C. ES/MS 168 (Cation C$_{11}$H$_{22}$N), −66 (Anion C$_2$N$_3$).

Example 7

Hexanedinitrile was hydrogenated in the presence of hydrogen gas and an iron catalyst at an elevated temperature of 140° C. and an elevated pressure of 4500 psig. Following the hydrogenation, the by-product azapane was separated from the main reaction product 1,6-hexanediamine by distillation at reduced pressure and elevated temperature.

The azepane by-product was then used to form ionic liquids of the present invention, for example by the processes in examples 1, 2, 5 and 6.

Example 8

2-methylpentanedinitrile was hydrogenated in the presence of hydrogen gas and a Raney cobalt catalyst at elevated temperatures of 115° C. and an elevated pressure of 800 psig. Following the hydrogenation, the by-product 3-methylpiperidine was separated from the main reaction product 2-methyl-1,5-pentanediamine by distillation at reduced pressure and elevated temperature.

The azepane by-product was then used to form ionic liquids of the present invention, for example by the processes in examples 3 and 4.

The invention claimed is:

1. An ionic liquid comprising a cation according to Formula I:

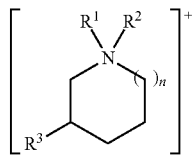

Formula I wherein:
  n is 2,
  $R^1$ is selected from the group consisting of: H, $C_1$-$C_{12}$ alkyl, and aryl or together with $R^2$ may form a heterocyclic ring, and
  $R^2$ is selected from the group consisting of: H, $C_1$-$C_{12}$ alkyl, and aryl or together with $R^1$ may form a heterocyclic ring, and
  $R^3$ is selected from the group consisting of hydrogen and $C_1$-$C_{12}$ alkyl, and wherein $R^1$ and $R^2$ are not simultaneously selected from hydrogen,
  the ionic liquid additionally comprising an anion $X^-$ selected from the group consisting of nitrates and silicates.

2. The ionic liquid according to claim 1, wherein $R^3$ is hydrogen.

3. The ionic liquid according to claim 1, wherein $R^1$ is a methyl group.

4. The ionic liquid according to any one of claim 1, 2 or 3, wherein $R^2$ is a butyl group.

5. The ionic liquid according to claim 1, which is composed of ions and is liquid at or below 100° C.

* * * * *